United States Patent
Novotny

(10) Patent No.: US 10,052,052 B2
(45) Date of Patent: Aug. 21, 2018

(54) OPTICAL SENSING ARRAY ARCHITECTURES FOR SPATIAL PROFILING

(71) Applicant: Vlad Joseph Novotny, Los Gatos, CA (US)

(72) Inventor: Vlad Joseph Novotny, Los Gatos, CA (US)

(73) Assignee: Vlad Joseph Novotny, Los Gatos, CA (US)

(*) Notice: Subject to any disclaimer, the term of this patent is extended or adjusted under 35 U.S.C. 154(b) by 64 days.

(21) Appl. No.: 14/306,228

(22) Filed: Jun. 17, 2014

(65) Prior Publication Data

US 2015/0362427 A1 Dec. 17, 2015

Related U.S. Application Data

(60) Provisional application No. 61/836,317, filed on Jun. 18, 2013.

(51) Int. Cl.
| | |
|---|---|
| A61B 5/00 | (2006.01) |
| A61B 5/1455 | (2006.01) |
| A61B 5/145 | (2006.01) |
| G01J 3/00 | (2006.01) |
| G01N 21/47 | (2006.01) |
| G01N 21/49 | (2006.01) |
| G01N 21/39 | (2006.01) |
| G01N 21/35 | (2014.01) |

(52) U.S. Cl.
CPC .............. *A61B 5/1455* (2013.01); *A61B 5/00* (2013.01); *A61B 5/14532* (2013.01); *G01J 3/00* (2013.01); *G01N 21/4738* (2013.01); *G01N 21/49* (2013.01); *A61B 5/0075* (2013.01); *G01N 21/39* (2013.01); *G01N 2021/3595* (2013.01)

(58) Field of Classification Search
None
See application file for complete search history.

(56) References Cited

U.S. PATENT DOCUMENTS

| | | | | |
|---|---|---|---|---|
| 5,721,612 A * | 2/1998 | Anderson | ............. | G01L 9/0079 356/35.5 |
| 5,949,532 A * | 9/1999 | Schrof | ............. | G01J 3/44 250/458.1 |
| 6,070,093 A * | 5/2000 | Oosta | ............. | A61B 5/0095 356/39 |
| 6,204,922 B1 * | 3/2001 | Chalmers | ............. | G01B 11/0616 356/630 |
| 7,087,901 B2 * | 8/2006 | Ambuel | ............. | G01N 21/359 250/339.01 |

(Continued)

*Primary Examiner* — Charlie Y Peng

(57) ABSTRACT

Multiple optical architectures based on photosensitive arrays are disclosed. The optical engines collect five dimensional data from the samples with three dimensional spatial information and temporal and spectral information simultaneously, in parallel from all channels, without optical scanning. The photosensitive arrays and/or last component of illumination system are in contact or close proximity of the sample surface. The application of optical engines to sensitive detection of species of interest in the complex reflecting and scattering matrix with the high concentration of interfering species is described. The optical engines are applicable to noninvasive, mobile monitoring of various species of interest in vivo and in vitro.

22 Claims, 13 Drawing Sheets

(56) References Cited

U.S. PATENT DOCUMENTS

| | | | | |
|---|---|---|---|---|
| 7,692,797 | B2* | 4/2010 | Kawahara | A61B 5/0066 356/497 |
| 9,222,832 | B2* | 12/2015 | Kulcke | A61B 5/14532 |
| 2003/0219891 | A1* | 11/2003 | Yazawa | C12Q 1/6825 435/287.2 |
| 2004/0233545 | A1* | 11/2004 | Jiang | G01N 21/6428 359/726 |
| 2005/0110989 | A1* | 5/2005 | Schermer | G01N 21/253 356/246 |
| 2005/0254058 | A1* | 11/2005 | Alphonse | A61B 5/0066 356/479 |
| 2006/0055935 | A1* | 3/2006 | Cheben | G01J 3/02 356/451 |
| 2007/0201031 | A1* | 8/2007 | Axelrod | A61B 5/02154 356/477 |
| 2011/0122407 | A1* | 5/2011 | Jalali | G01N 21/65 356/301 |
| 2011/0176146 | A1* | 7/2011 | Alvarez Diez | G01B 11/002 356/601 |
| 2013/0100439 | A1* | 4/2013 | Yu | G01N 21/255 356/73 |
| 2013/0289362 | A1* | 10/2013 | Kruglick | A61B 5/0059 600/301 |
| 2014/0155760 | A1* | 6/2014 | Ridder | A61B 5/6835 600/479 |
| 2014/0231635 | A1* | 8/2014 | Kerness | G01S 17/026 250/226 |
| 2015/0260645 | A1* | 9/2015 | Joo | G01N 21/171 356/40 |

\* cited by examiner

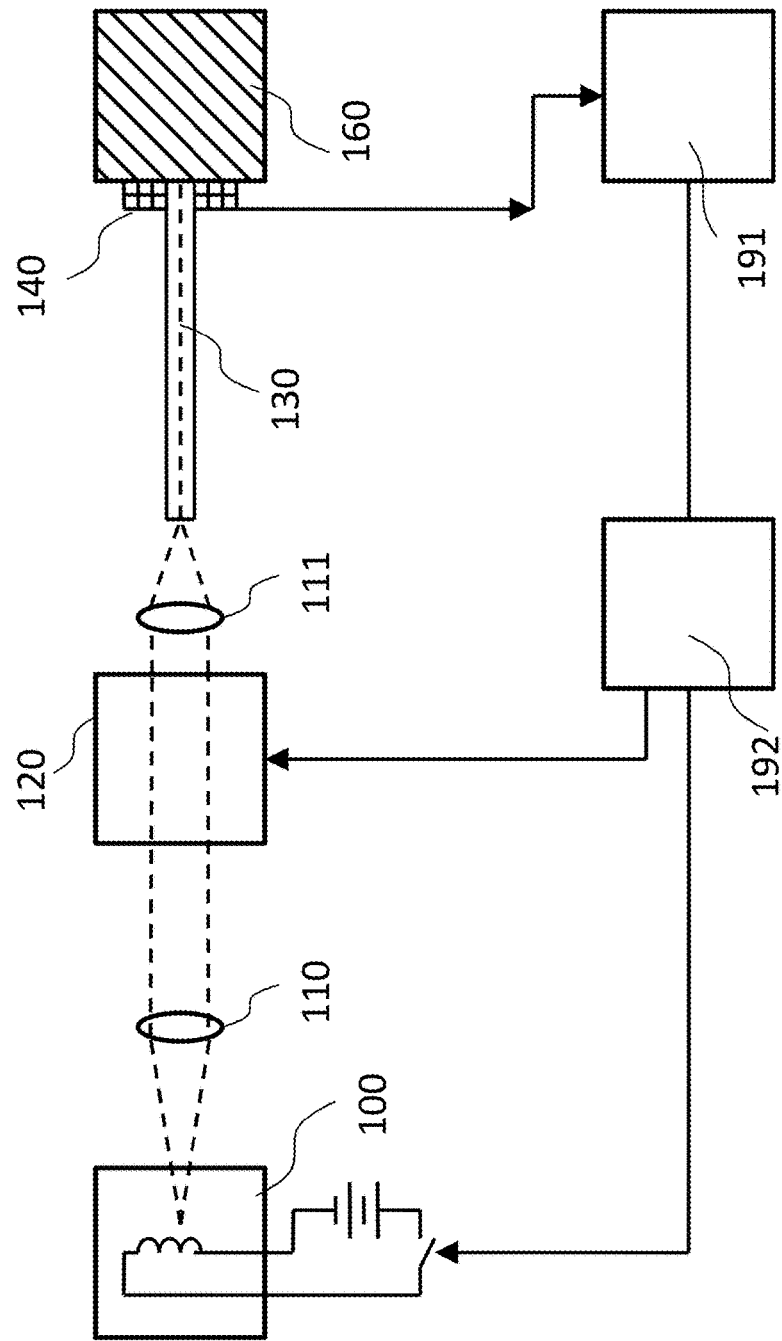

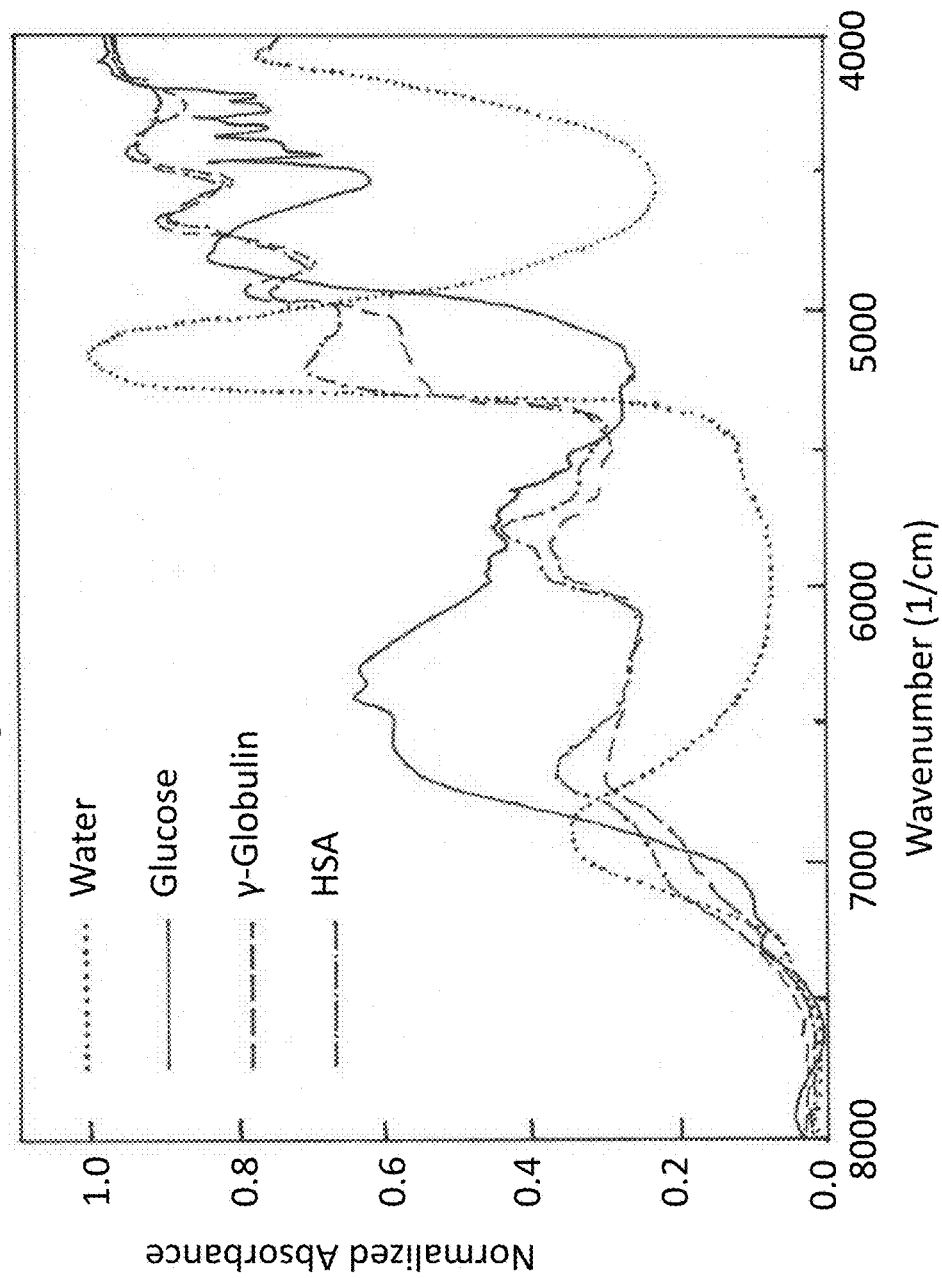

OPTICAL SENSING ARRAY ARCHITECTURES FOR SPATIAL PROFILING

RELATED U.S. APPLICATION DATA

Provisional application No. 61/836,317 filed on Jun. 18, 2013.

BACKGROUND

This description relates to non-invasive optical architectures of sensors for quantitative and sensitive detection of low concentration of species of interest in complex matrices that have significant specular and diffuse reflection and interfering signatures in the measured spectral regions. These sensors have to be invariant to changes in the background signals, changes in temperature and relative humidity, separation between the measured sample and the sensor surface, contact pressure at sensor-sample interface and other variable factors. In addition, the sensors should have small volume, low power requirements, be insensitive to mechanical disturbances and easy to use in mobile applications.

One example of the application of this technology is non-invasive detection of glucose by measurements through the skin in dermis and subcutaneous layer. Another example of the application of this device is monitoring of quantitative level of infection and/or healing in subsurface regions of the body in order to make decisions about non-invasive or invasive treatments. Yet another example is detection of subsurface contaminants in food items before buying them or consuming them.

SUMMARY

Multiple optical architectures are described for very sensitive detection of species of interests in the complex scattering matrix with the high concentration of interfering species and presence of high level of specular and diffuse reflectance background. The disclosed optical engines reject efficiently reflectance background light, have very high optical signal collection efficiency and collect five dimensional data from the samples with three dimensional spatial information without any optical scanning, temporal information and spectral information. The engines are applicable to non-invasive, mobile monitoring of various species of interests in vivo and in vitro.

DESCRIPTION OF DRAWINGS

FIG. 1a: Schematic diagram of the optical engine architecture with array of optical sensors contacting the sample surface and Fourier Transform interferometer using center fiber optic illumination.

FIG. 11a: Near infrared spectra of glucose, water and common interferants.

DETAILED DESCRIPTION

Figure 1B:
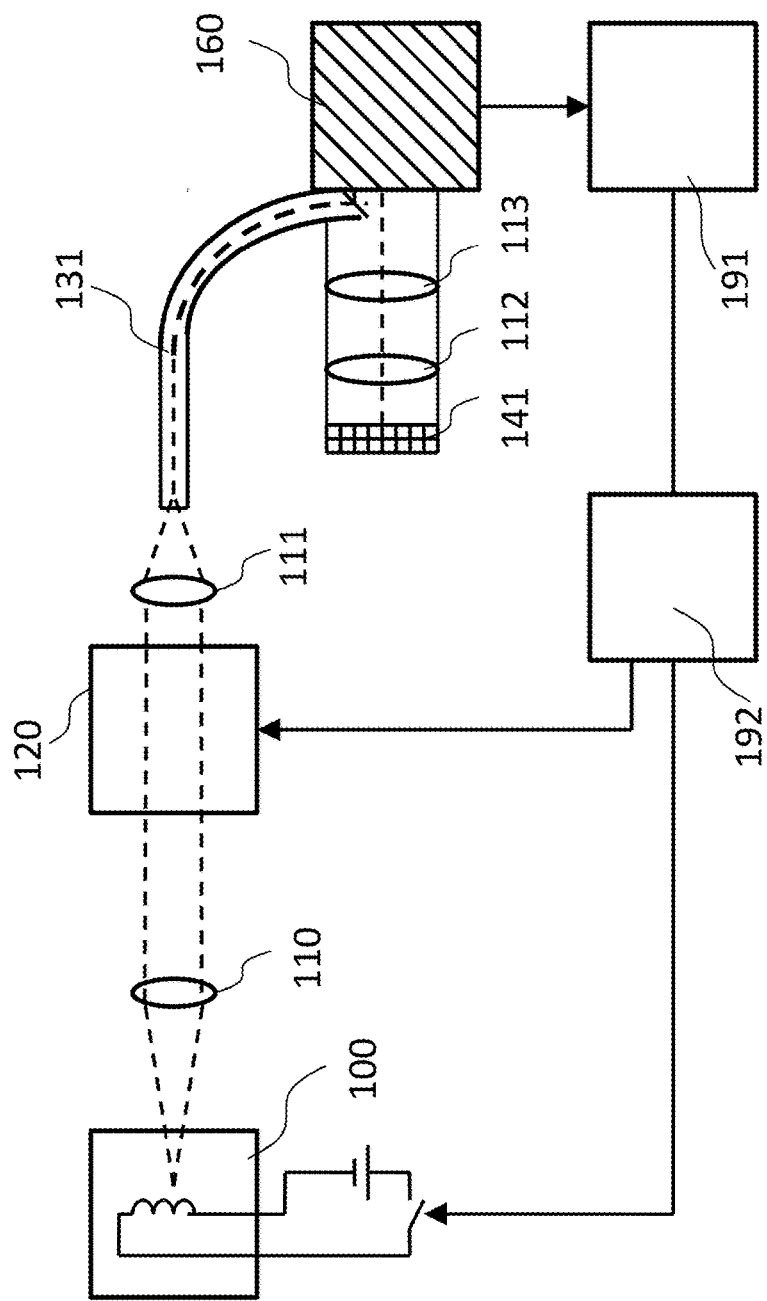
FIG. 1b: Schematic diagram of the optical engine architecture with non-contact array of optical sensors and Fourier Transform interferometer using center fiber optic illumination.

The operational principle of the non-invasive optical detection of specific chemical and biological species relies on quantitative measurements of optical absorption of these species as a function of spatial position in three dimensions, it means as of function x, y and z where z is in the direction normal to the surface of the sample. In order to obtain the accurate concentrations of these species in inhomogeneous and highly scattering matrix, the multiple spectral measurements need to be done using different optical paths. The usual way of performing this type of data acquisition is to vary spatial positioning between the illuminated locations and detector placement by scanning the position of the illumination beam(s), including the depth profiling in z direction. Alternatively, the illumination beam can be held fixed and the detector can be scanned or moved. These approaches require sequential, spectral data acquisition from different spatial locations, including depth. In addition, they require complex optical hardware, have large optical losses and result in poor signal to noise ratio and inadequate detectability limits for species of interest.

The species of interest are often present at very low concentrations in the presence of high level of strong scatterers and high concentration of other absorbing species that have significant or dominant optical absorption in the same spectral regions. At the same time, it is required to acquire this spectral and spatial optical absorbance data on short time scales, in effect capturing the spectral dynamics of these species. Overall, data should be acquired in five dimensions—three spatial dimensions x, y, and z, and as a function of time and wavelength.

The spectral, spatial and dynamic data is required because of effect of interferants that dominate the spectra, effect of scatterers and spatial variability of concentration of many absorbing species that have to be unraveled from the signal of interest by sophisticated digital signal processing that uses these various dependences. This description does not address the preferred ways of signal processing; it deals with the optical engine architectures that enable the acquisition of data with high signal collection efficiency and rejection of background signals without mechanical or optical scanning.

The central feature of these optical architectures described below is an array of optical detectors preferably in contact with the measurement media and the single stationary beam or multiple, stationary illumination beams. Another feature of these architectures is the detector array or illumination element in physical contact or close proximity with the sample surface which can be rough and inhomogeneous optically. Such surfaces generate large, specularly reflected and diffusively scattered signals that are distributed over full half solid angle and cannot be easily rejected from the signal of interest. Consequently, the optical background signals can totally swamp relevant signals of interest. In the proposed architectures, no spatial scanning is required while the three dimensional (3D) profiling is accomplished. The optical data is acquired simultaneously in parallel from many channels, yielding data for multiple optical paths with variable depth and surface positions.

The optical engines described here have typically three modules—light source, optical interferometer and optical sensor array. Schematic diagram of the first optical engine architecture with array of optical sensors contacting the sample surface, Fourier Transform (FT) interferometer and center illumination is shown in FIG. 1a. This spectral, spatial and dynamic detection of diffuse reflectance from the sample relies on use of FT interferometry, the black body radiation light source, fiber optic illumination and sensor array in contact with the sample. The black body is broad wavelength light source that can provide adequate level of illumination from 200 nm to 10000 nm, depending on the temperature of the tungsten filament. The light emitted from the filament is collected by the optical components 110 that collimate the light and direct it onto the entrance opening of the interferometer 120 such as Fourier Transform InfraRed (FTIR) type shown in FIG. 1a. The light from the interferometer is coupled by optical components 111, into the illumination fiber 130 that brings the light to the surface or subsurface of the sample 160. The interferometer can be of conventional Michelson type with beamsplitter, movable mirror and stationary mirror or integrated fiber optic Mach-Zehnder type, Rippel Jaacks type or other interferometer. For mobile applications, the interferometer should be small and require low power consumption. In a small Michelson interferometer, it is difficult to maintain low tilt and tip of the moving mirror. Two cube corner double pendulum architectures such as Rippel and Jaacks are preferable because they are insensitive to tip and tilt and vibrations. The moving components can be driven by small, low power electrostatic actuator or electromagnetic actuator built using Micro Electro Mechanical Systems (MEMS) or voice coils.

The diffusely reflected optical signals from the sample 160 are detected by the sensing array 140. The background specularly and diffusely reflected light from the sample surface is not collected and not detected by the sensing array. In addition, with the center illumination with respect to the symmetrically distributed array around the illumination beam, all light in half solid volume can be in principle collected with the large enough sensing array. The conventional collection of detected light gathers usually a very small fraction of light from available half solid volume. This configuration provides significant advantage compared with other optical architectures as the maximum collection efficiency (in principle up to 100% of the half solid volume, i.e. half sphere solid angle of $2\pi$) can be achieved. In contrast, the conventional collection of detected signal with fibers or lenses allows background light to flood the detector with unwanted signals, buries the signal of interest and detects only a fraction of available signal.

For detection in infrared region from about 800 nm to 2500 nm, the detector array can be based on InGaAs materials with or without extended range or PbS, PbSe or HgCdTe materials or microbolometers that have very broad spectral response. When the detection is focused on the ultraviolet, visible and near infrared (up to 1000 nm) spectra acquisition, the detector array can be silicon photodiode based.

The signals from the detectors are amplified and digitized with analog-to-digital converters that are incorporated into the Read Out Integrated Circuit (ROIC) that is fabricated under the sensor array 140. The electrical digital signals are fed into the data acquisition system 191 and then into the controller and signal processor 192. The controller 192 synchronizes the operation of the rest of the components of the engine, in particular turning on and off the light source 100, operation of FTIR interferometer 120 and collection of digitized data from the ROIC array in 140. The digital electrical signals are analyzed with the digital signal processor 192, including FT computation, averaging, scaling and storage of spectral data. The maximum acquisition and processing efficiency is achieved with these architectures as all spectral data are collected and processed in parallel, allowing the fastest data acquisition. The capture of time dependent phenomena is limited only by scanning frequencies of the interferometer 120. When interferometer is based on MEMS, high scanning resonance frequencies can be obtained, resulting in very short scanning and acquisition times.

One variant of the optical architecture of FIG. 1a is shown in FIG. 1b. The key difference between the architecture in FIG. 1b and one in FIG. 1a is the placement of the detector array. The detector array 140 in FIG. 1a is in contact with the sample surface while the detector 141 in FIG. 1b is displaced from the sample surface and optical signal is collected from the sample using the optical components such as a set of lenses 112 and 113. In order to minimize the collection of light scattered from the sample surface, the illumination fiber is in contact with the sample surface. To minimize interference of the fiber on the signal of interest, the fiber is brought parallel to the surface and the light is re-directed 90 degrees to the sample with the angled, reflecting surface or similar optical element. The optical collection efficiency is not as high with the architecture in FIG. 1b as it is with FIG. 1a architecture, but this system does not require any optical window between the sensor array and the sample surface. The architecture in FIG. 1a normally includes the window as detector surfaces should not be in direct contact with sample surfaces such as skin that contain oils, particulates and contaminants. The sensitive detector surfaces can be contaminated or damaged by electrostatic discharge without the window. The window can be easily cleaned if it is contaminated. The window has to be segmented in order to avoid optical cross talk, as described below.

Figure 2:
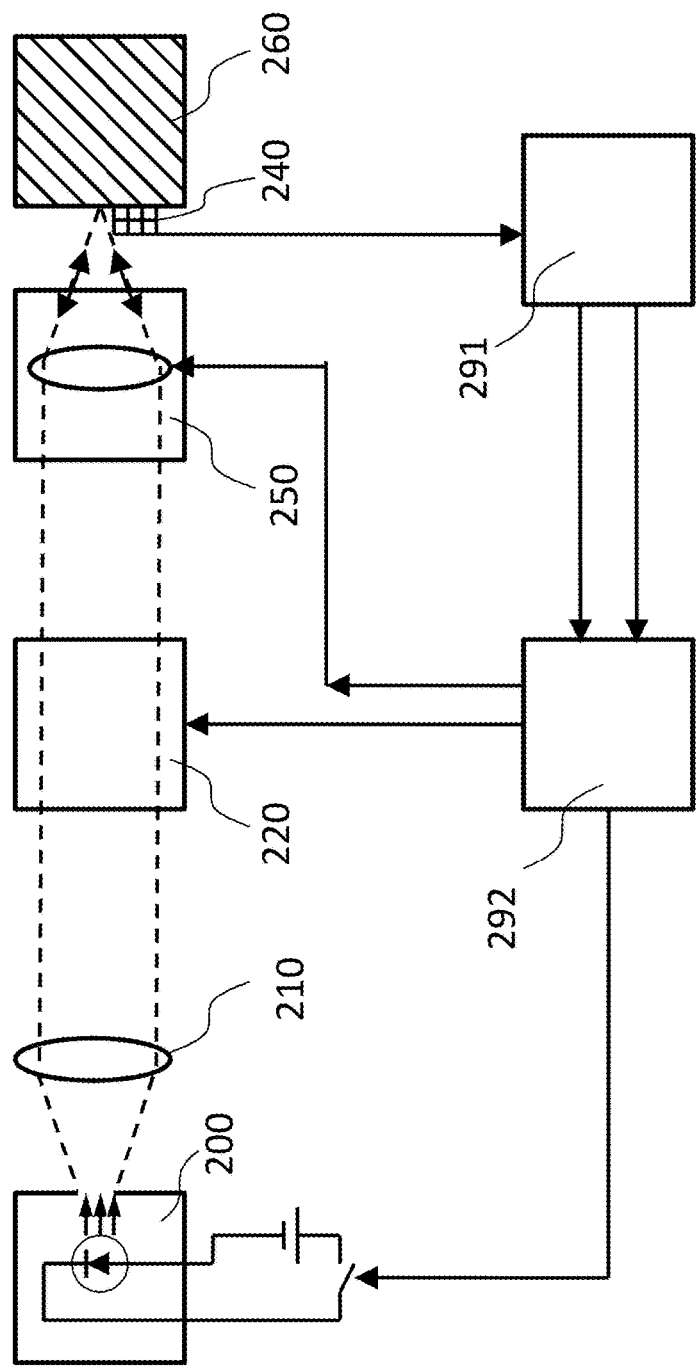
FIG. 2: Schematic diagram of the optical engine architecture with array of optical sensors contacting the sample surface and Fourier Transform interferometer using edge free space illumination with optional depth profiling.

Another optical architecture of interest for acquisition of spectral, spatial and dynamic data from the highly complex matrix containing efficient scatterers, high concentration of interfering species and low concentration of species of interest is depicted in FIG. 2. The optical engine in FIG. 2 is similar to the engine in FIG. 1 where the light source 200, interferometer 220, data acquisition system 291 and the controller with processing electronics 292 can be the same or similar. The differences lie in the illumination assembly 250, the sensor array 240 and the light source 200. The blackbody radiation light source 100 of FIG. 1 is substituted by Light Emitting Diodes (LED) or laser in combination with several fluorescent materials that are combined at right proportions to provide the high, desired fluorescent light intensities in the most relevant spectral regions. The free space, noncontact illumination with optional z direction movable lens in the assembly 250 can focus the light at the surface of the sample 260 or below the surface and provide more direct depth profiling. The sensor array 240 allows the edge, corner or center illumination. When the detected signal spatial distribution has at least two fold symmetry, then the sensing array needs to capture only quarter solid volume (solid angle of $\pi$) of signal without any loss of data while the smaller sensor array is used compared with sensor array in FIG. 1. When the detected signal spatial distribution has four fold symmetry, then the sensing array can occupy only quarter area without loss of data while the smallest sensor array is used.

The fiber illumination described in FIG. 1 can also be employed with the edge, corner or center illumination. Even though the optical architectures in FIGS. 1 and 2 have a single illumination beam, multiple illumination beams can be employed to optimize signal acquisition with these engines.

Figure 3:
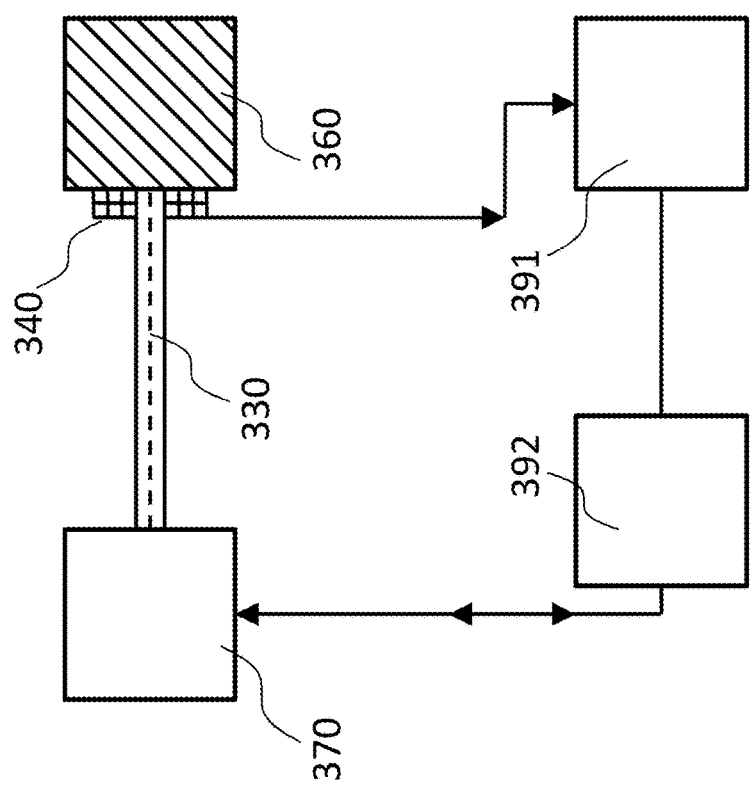
FIG. 3: Schematic diagram of the optical engine architecture with array of optical sensors contacting the sample surface and tunable narrow band light source or broadband light source.

The third and fourth optical architectures with contact sensing array for sensitive and quantitative detection of species in complex, nonuniform matrices with significant interference are shown in FIG. 3. The third and fourth optical architectures have common components, in particular the sensing detector array 340, acquisition system 391 and the controller plus processing unit 392.

In the third optical architecture, the spectrometry is accomplished with the tunable light source 370 such as broadband light source with tunable filter, Near Infrared (NIR) tunable laser or Mid Infrared (MIR) Quantum Cascade Laser (QCL) in conjunction with tunable diffraction grating. At present, Superluminescent Light Emitting Diodes (SLD) with tunable filters or NIR tunable lasers cover the spectral range from about 700 nm to 2000 nm, while QCL devices are available in the spectral range from about 3 um to 15 um in MIR range. They deliver very high power compared with other light sources such as black body radiation. They can be operated in pulsed or continuous modes, enabling dynamic studies more effectively than the architectures described in FIGS. 1 and 2. The light from the tunable light source 370 is delivered with the free space optics or fiber optics to the sample 360 with the last optical component of illumination optics 330 that is in contact with the sample surface or in non-contact mode. The sensing array 340 is in contact or in proximity with the sample surface as described for the architectures in FIGS. 1 and 2. When the tunable light source 370 operates in the NIR range, then sensing array uses InGaAs or PbS photosensitive materials described above, while in MIR range, the sensing array can be based on HgCdTe or other photosensitive materials or on microbolometer technology that senses light intensities thermally. All optical components, including windows and antireflective coatings, have to be transparent in the spectral region of interest. For MIR spectral range, ZnSe or germanium or other optically transmitting components are used. The details of the sensing array are outlined below. The digitized signals from the sensing array 340 representing the spatial map of localized light intensities are transferred into data acquisition system 391. The resulting data is moved into data processing unit and controller 392 that synchronize the operation of tunable light system 370 and data acquisition and analyze the data in situ or in the cloud after transmitting it into more powerful data processing system.

The fourth optical architecture illustrated in FIG. 3 has the broadband light source 370 and the filter array added to the sensor array 340 on the top of the sensor array. The filter arrays described in more details below, allow spectral acquisition without interferometer or tunable light sources. Each block of the sensor array that collects light for the similar, but not identical, optical paths has the full array of optical filters for the desired spectral region and resolution. These arrays of optical filters are repeated for each pseudo identical optical path, providing spectra corresponding to multiple optical paths. The minor differences between optical paths within one full block of filter arrays are taken into account in the data processing of absorption signals from the sample of interest.

The use of black body light sources, LED's, SLD's, lasers, tunable lasers or lasers in combination with a set of optimized fluorescent materials in FIGS. 1, 2 and 3 architectures is optional and selection is made depending on the spectral range that needs to be covered, required sensitivity, power consumption and the size and cost of the system.

Figure 4:
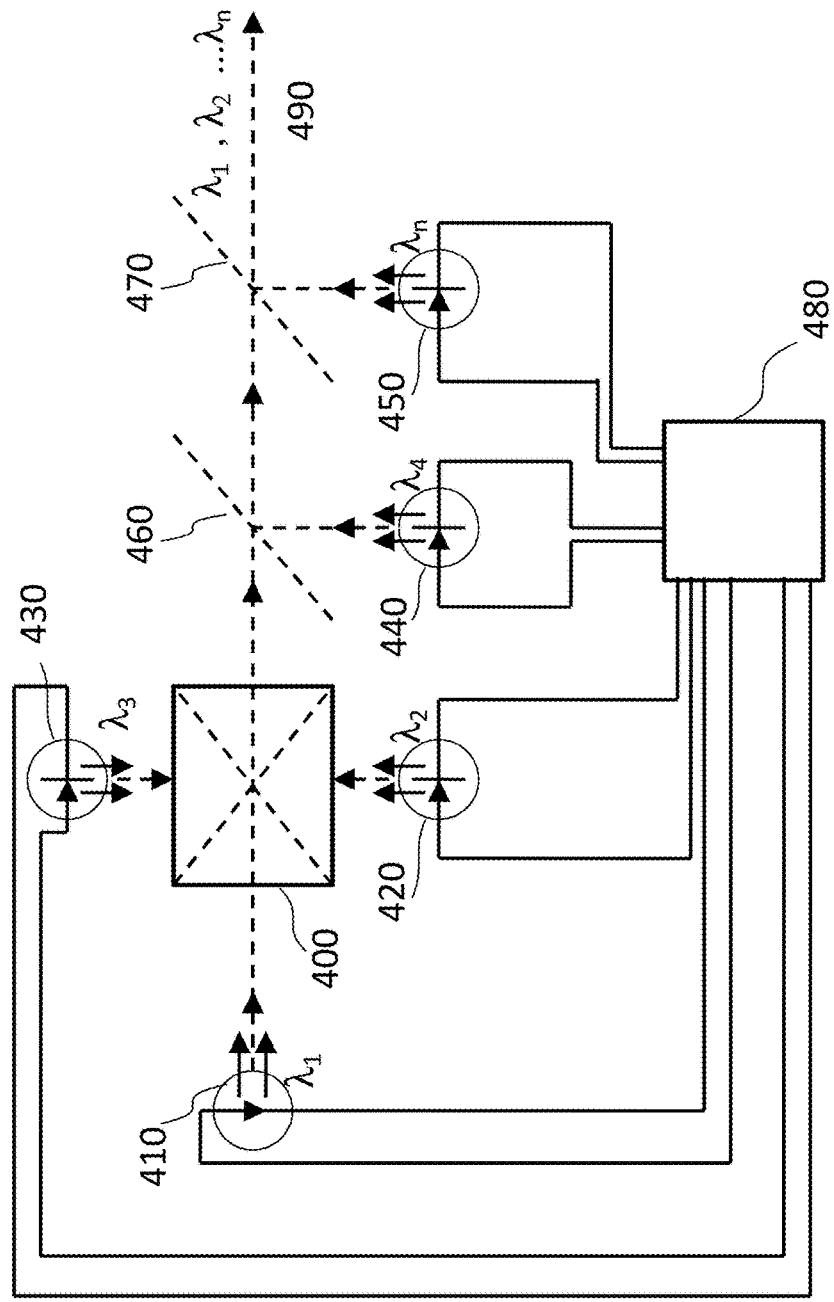
FIG. 4: Schematic diagram of the broadband light source consisting of multiple light sources with complimentary spectral coverage.

When SLD's, LED's or lasers are used, generally arrays of these light sources are required because relatively wide spectral range is needed while these sources have relatively narrow spectral ranges. The architecture of a light source with multiple SLD's, LED's or lasers is shown in FIG. 4. The light from these multiple sources is coupled together with an array of cube combiners 400 and/or linear combiners 460, 470, etc. The light sources 410, 420 and 430 with the central wavelength $\lambda 1$, $\lambda 2$ and $\lambda 3$ are placed around the combiner cube 400 and additional light sources 440, ... 450, if required, are arranged so that they are combined using the linear array of beamsplitters/combiners 460, 470 into the light source that covers the central wavelengths $\lambda 1$, $\lambda 2$, $\lambda 3$, $\lambda 4$, ... $\lambda n$. The power supply 480 energizes the light sources 410, ... 450 all at the same time for continuous or pulsed operation or sequentially for continuous or pulsed sequential operation. The resulting beam contains the light spectra spreading over the desired range of wavelengths.

Figure 5:
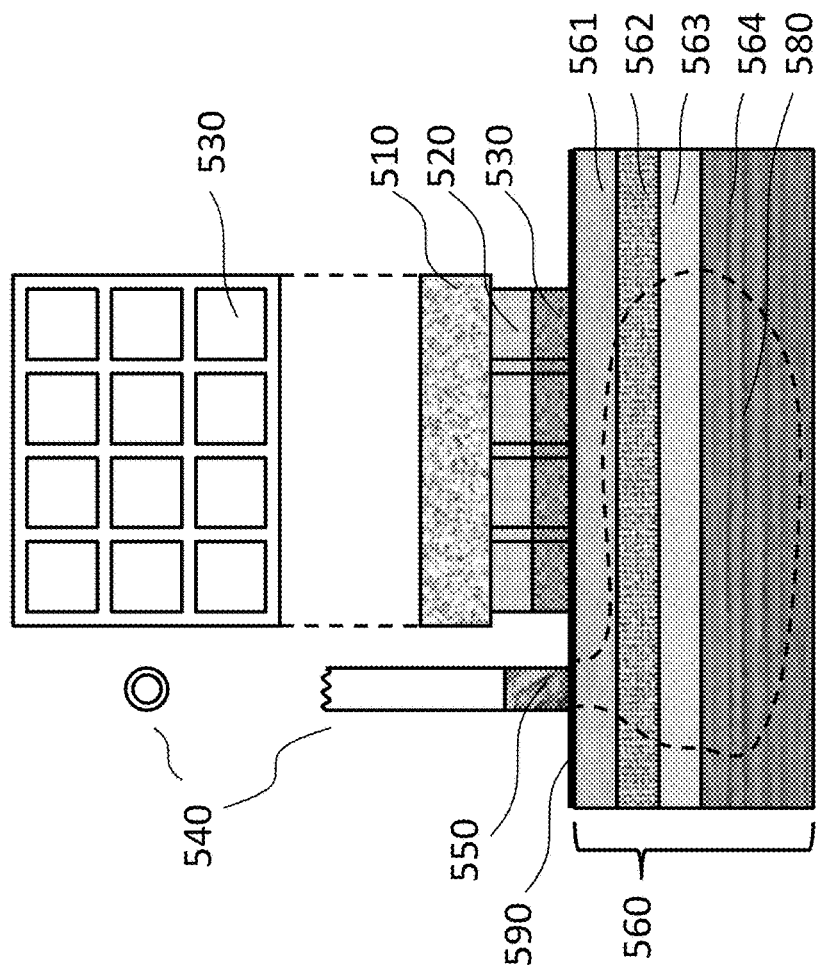
FIG. 5: The top and side view diagram of the sensor array in contact with the sample surface and its relationship to asymmetric edge illumination using the optical fiber and grin lens in contact with the sample surface.

The details of the sensing array 500 are shown in FIG. 5, where 3×4 array is illustrated, even though any size of the array can be conveniently used. The example in FIG. 5 is given with the fiber optic edge illumination with fiber 540 in contact with the sample surface 590. The optical fiber 540 can be bare or terminated with light shaping components such as grin lens or refractive or diffractive lens that allows most of the light to be directed asymmetrically into region 580 under the sensing array. The illustrated sample is skin 560 with stratum corneum 561, epidermis 562, dermis 563 and subcutis 564, but any sample can be monitored. The real skin surface has very significant roughness and is heterogeneous which is not shown in the drawing. The roughness, multilayer structure and heterogeneity of the skin lead to significant specular and diffuse light scattering. The surface scattering which presents the major contribution to the undesirable optical background is completely eliminated in this contact sensor configuration. In order to minimize optical losses of detected signals at skin-sensor (or window) interface, the refractive index matching liquid (such as fluorinated liquid for measurements on skin) can be optionally included.

The sensor array 500 is configured so that the photosensing array 530 (or window covering the array that is not shown) is in contact with or in close proximity to the skin surface, followed by the ROIC Complementary Metal Oxide Semiconductor (CMOS) array 520 and the substrate 510.

Figure 6:
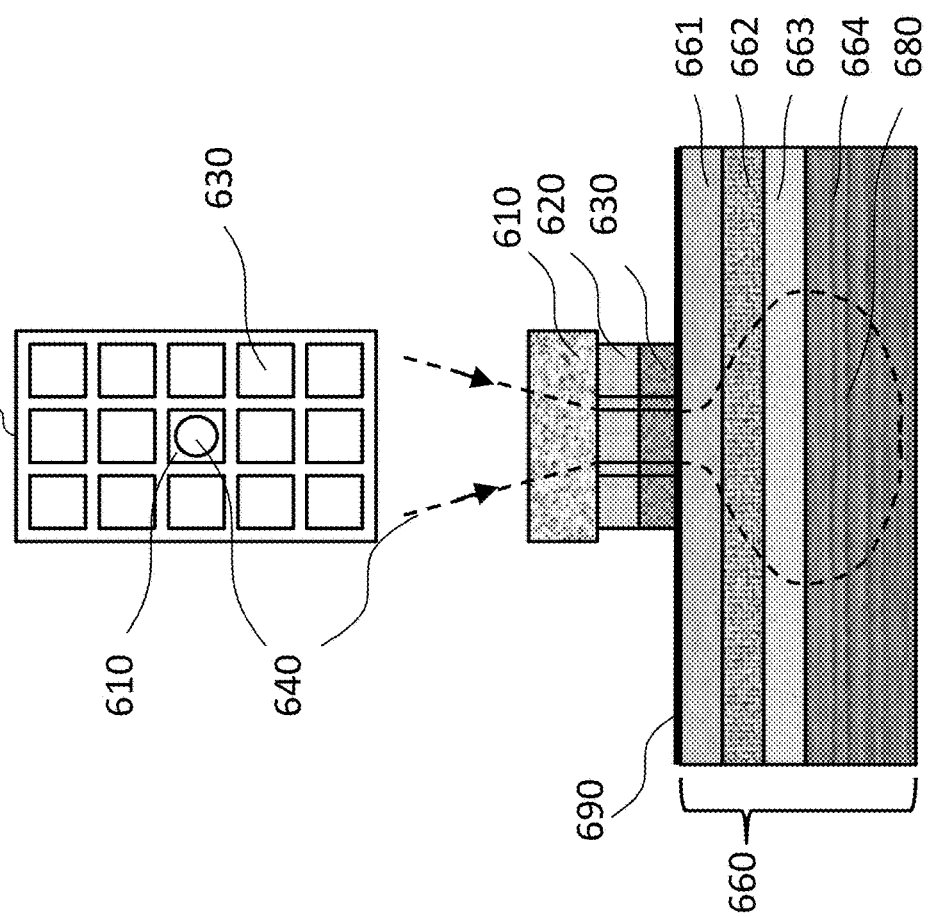
FIG. 6: The top and side view diagram of the sensor array in contact with the sample surface and its relationship to center light illumination using the noncontact free space optics.

The FIG. 6 shows the optical configuration with the central, free space illumination 640 and 3×5 sensing array 600. The majority of components is the same as described in FIG. 5, including the photosensitive array 630, ROIC array 620, sensing array substrate 610, the skin 660 with stratum corneum 661, epidermis 662, dermis 663, subcutis 664 and optional refractive index matching liquid. The central illumination 640 is directed from the sensing array sample substrate 610 and reasonable optical transparency of the substrate in the spectral range of interest or physical opening is required. When illumination light passes through the substrate 610, the ROIC stack 620 and photosensing multilayer 630, then these layers need to have good optical transparency. Optionally, this region can be masked during deposition and/or etched away during the fabrication generating clear opening for incoming light. The spreading of illumination beam and diffusely reflected light pattern containing absorption data of the measured species of interest is also illustrated schematically in the FIG. 6, as the region 680.

Figure 7:
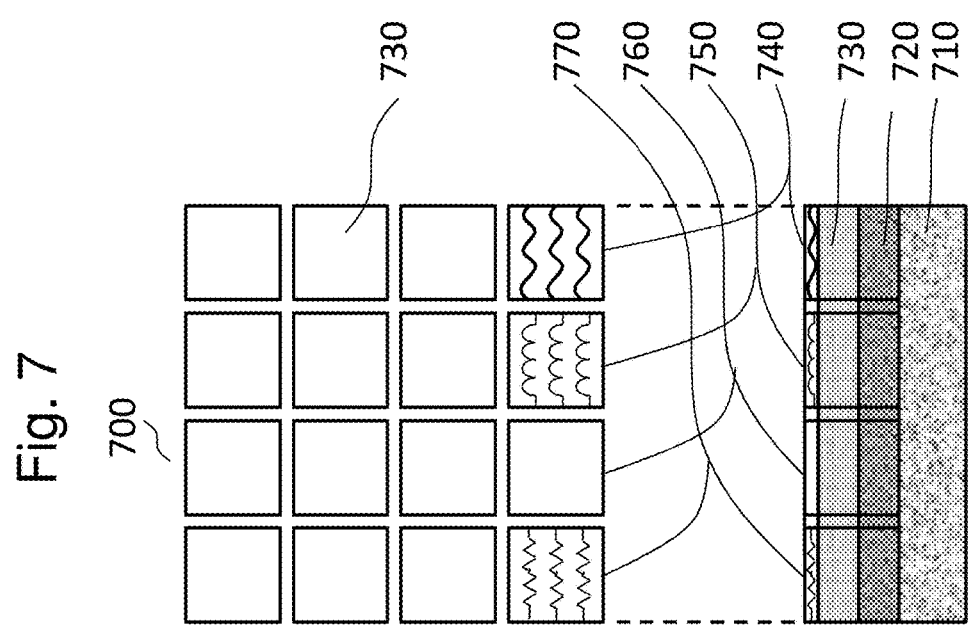
FIG. 7: The details of the sensor array with array of optical filters positioned over the photosensitive surface permitting acquisition of spectra without dispersive or interferometric optical devices.

Another version of sensing array 700 is depicted in FIG. 7. The array 700 has the similar features as the arrays in FIGS. 5 and 6, except the photosensing elements 730 in the array 700 are not the same. The individual elements 730 have optical filters 740 fabricated over the photosensitive areas, thus providing the spectral filtering without the use of the interferometry, dispersive spectrometry or tunable light sources. This type of filter array is employed in the fourth optical architecture of FIG. 3. The simplest filter array can be composed of color filters, but such filters have relatively poor spectral resolution because the filter transmission is relatively broad. The interferometric filters, such as those of Fabry Perot (FP) type, can deliver high spectral resolution that is defined by the construction of the filters. The simplest filters of FP type contain a single cavity whose thickness defines the central wavelength of the transmitted light and two stacks of multilayers above and below the cavity that are composed of one or more sets of layers of alternating high and low refractive indices. The transmission bandwidth depends on whether there are multiple repeating structures with multiple cavities.

The interferometric transmission characteristics are strongly dependent on the incident angle and the spectral resolution can be maintained only when the incident angle range is controlled. This requirement is accomplished by addition of the segmented window that contains as many window frames as there are interference filters and detectors. The window frames employed with filter arrays have to have strong light absorption to control the incident angle of light falling on the interferometric filter in a narrow range. Further improvements of spectral resolution are obtained by data processing of the optical signals in the large array of sensors and filters as the light propagation from the illumination point to the sensors has consistent spatial patterns.

The preferred embodiment of the sensor array with the window but without filter array is with the segmented window. Such segmented window eliminates the optical cross talk between the sensor elements. Diffusely reflected light has the optical rays with varying angles of incidence on the window surface which would allow them to propagate in the waveguiding manner through the window plate. Consequently, the light beam falling on any given window section would refract at the window interface, propagate with multiple reflections into surrounding sensors and lead to optical cross talk. The reflecting frames in the window structure, as opposed to absorbing frames required with the filter arrays, confine the light within individual sensors, preserve the light intensity without significant losses and prevent waveguiding propagation.

Figure 8:
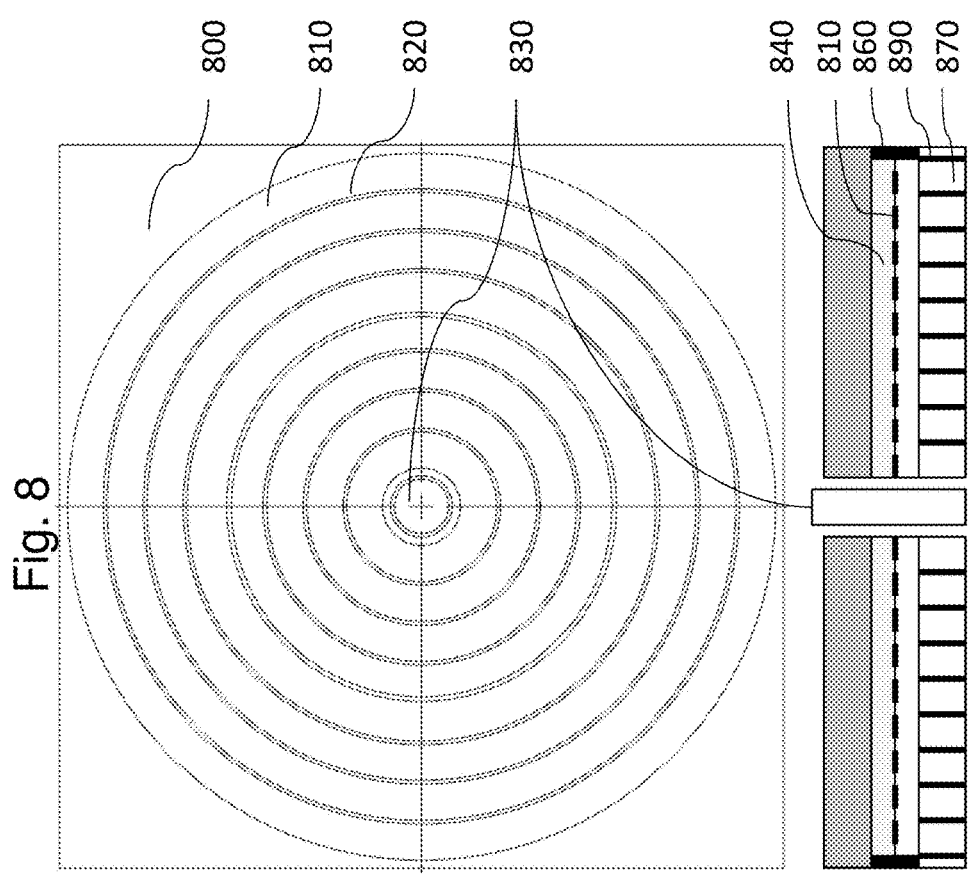
FIG. 8: The radial sensor array with central optical fiber illumination and segmented window that can be implemented with discrete readout electronics.

The design of the segmented window is illustrated in FIG. 8. This example is shown with the sensor array that is formed by radial pattern of photodetectors 810 separated by gaps 820 around the central fiber illumination 830. This sensor configuration can be used when the optical diffuse reflectance signals are circularly symmetric and when actual patterns of diffuse reflectance are not required. The segmented window 870 is shown in cross section in FIG. 8. The photodetector array 810 is separated from the segmented window 870 by the spacer 860 for cooled sensors. In that case, the sensor array can be at different temperature than the sample surface, such as skin. The space between the detector array 810 and segmented window 870 can be at vacuum or low pressure. When the detector array can be operated at the same temperature as the sample, then the spacer 860 and gap are not required. The radial pattern detector array can have integrated ROIC 840 underneath the sensors or can have the separate discrete electronics. The radial detector array can have complete circular elements as shown in FIG. 8 or these elements can be subdivided into angular segments when the sample does not have the complete circumferential symmetry and exhibits directional diffuse reflectance pattern.

When the number of sensing elements is not too high, as illustrated in the example in FIG. 8, the stacked integration of ROIC array with the sensor array is not required. The amplifiers and digitizers on the separate CMOS chip can be employed. They can be connected to the sensors with electrical leads between the electrical pads placed on chip 800 and sensors 810 and additional electrical leads between these electrical pads and the separate CMOS electronics. The electrical leads on the chip have to be electrically isolated from the sensor surfaces 810 that are being crossed except the targeted ones by adding the insulating patterns or the unpatterned insulating film between the sensor surfaces 810 and the electrical leads. These electrical leads and insulating layers can be added below or above the sensing structure. This optoelectronic configuration does not require stacked sensor-CMOS ROIC integration and is compatible with optical architecture of FIG. 1b with non-contact detector. This integration option does not have as high quality of electrical signals due to higher noise when the sensors are connected with longer electrical leads to external electronic circuits.

The segmented window with frames can be fabricated by several processes. One process for the segmented window used with the sensor arrays relies on coating glass fibers with reflecting material, assembling fibers into large bundles, fusing the fibers together and optionally filling the space between the fibers. Subsequently, the fused fiber bundles are cut into the large plates, forming the segmented windows. The fabrication process for segmented window used with the interferometric filter array starts with assembly of capillaries. This process is similar to microchannel fabrication. The capillaries are assembled into the large bundle and subsequently fused together. Next, the fused bundle is sliced into wafer plates that are coated on the inner walls of capillaries with light absorbing material. Another process for fabrication of the segmented windows starts with lithographic patterning of the wafer plate. The deep reactive etching or sandblasting creates openings in the window plate where there is no photoresist coverage. Subsequently, the inner walls are coated with the suitable light reflecting or light absorbing material. The frame structure can be alternatively formed by injection molding or by ultrasonic machining using the patterned plate. The diffractive or refractive lens structures can be added on the entry side of the plate to adjust the acceptance angle of light into the window.

Interferometric filter arrays with narrow spectral transmission are fabricated by micromachining techniques. When the spectral region is not too wide, then only cavity dimensions have to be strictly controlled for individual filters. The quarter wave layers of alternating of high and low refractive indices that form the mirrors surrounding the cavity can be of the same thicknesses for different filter elements in intermediately wide spectral range. For very wide spectral range of filter arrays, these quarter wave layers have to have optimized thicknesses. The pattern of variable thickness of cavities or mirror stacks is produced lithographically with or without photomasks. After deposition of the layer that has to be patterned with variable thicknesses, one option is to use gray scale lithography to define the desired pattern of elements with variable thickness during the subsequent etching step. Another fabrication option is to selectively etch the pattern using photoinduced chemical etching or chemical ion beam etching or electron beam controlled etching.

The typical materials used in fabrication of the interferometric filters are silicon dioxide $SiO_2$ for low refractive index material and tantalum pentoxide $Ta_2O_5$ for high refractive index material. The cavity material can be either high or low refractive index material. Other materials with high refractive indices such as hafnium oxide $HfO_2$ or zirconium oxide $ZrO_2$ and low refractive indices such as magnesium fluoride MgF can also be used.

The photosensors with filter arrays can have up to 10,000 to 100,000 elements, pixel dimensions in 10 um range and the overall chip dimensions 1000 to 3000 um. At another extreme, the relatively small arrays (3×3 to 8×8) with pixel dimensions of hundred of microns are also of interest. They result in the sensing chip dimensions of about 500 um to 3000 um. Even though the specific dimensions are included here, the number of sensing elements in the arrays and their dimensions do not have any particular limitations.

The range of spectral sensitivity of photosensors in the array can be also varied during their fabrication. In case of InGaAs type arrays, the sensitivity cutoff range can be varied between 1.7, 1.9, 2.2 and 2.6 um. Alternatively, the filter arrays can be incorporated as described above for these arrays.

Figure 9:
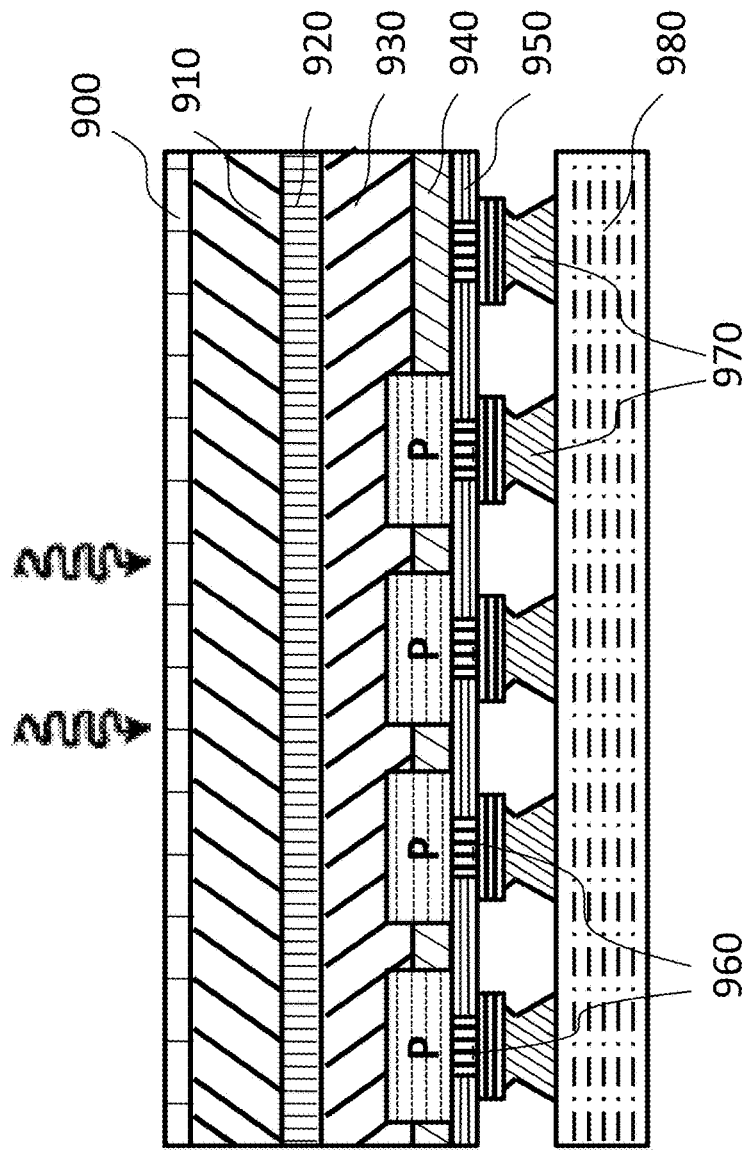
FIG. 9: The cross sectional diagram of the sensor array with photosensitive structure fabricated over or bonded to the readout integrated circuit.

The detailed cross sectional structure of hybrid arrays with photosensitive InGaAs elements bonded to ROIC is shown in FIG. 9. The basic photosensing structure is PIN (p doped-insulator-n doped) type in which the insulator layer is the light absorbing film. Starting with the $n^+$ InP substrate 910, $n^+$ InP epitaxial layer 920 is grown first. Next, intrinsic i InGaAs film 930 that serves as the photosensitive layer is deposited epitaxially. Then, another film 940 of $n^-$ InP is deposited and patterned. The patterned regions are p doped to serve as the electrical contacts to the basic PIN structure. The surface is passivated with the layer 950 to protect the structure. The areas above p regions 960 and at least one area of $n^+$ InP type are opened up and metalized to make the electrical contacts to the structure. In the last step of sensing wafer fabrication, AntiReflective Coating (ARC) single layers or multilayers 990 are applied on the substrate surface 910.

Separately, ROIC's are built on different wafers using the conventional CMOS processing. Subsequently, indium bumps 970 are deposited on metalized areas either on the sensor or ROIC wafers. The last step of fabrication involves bonding of the sensing wafer to ROIC wafer using indium bumps that form electrical contacts and mechanical connections between individual sensors and individual circuits.

Normally, these devices are packaged with the windows for vacuum or low pressure environment so that devices can be cooled from the substrate side for performance with lower dark currents and improved signal-to-noise ratio. The preferred packaging embodiment is with Wafer Level Packaging (WLP) in which the sensing wafer bonded with ROIC wafer is in turn bonded at the wafer level to window wafer and then singulated into the individual chips. The packaging can be performed also by singulating sensing+ROIC wafer into individual chips and then packaging them individually.

In principle, the monolithic arrays of photosensors integrated with ROIC's can also be fabricated. In this case, the electrical circuitry is fabricated first and subsequently photosensitive detector array is added on top of ROIC. The temperatures during processing of photosensitive array cannot exceed temperatures allowed for ROIC. InGaAs arrays require high processing temperatures and then the ROIC has to use GaAs integrated circuit technology. When the sensitive arrays are based on microbolometers, the underlying ROIC can be conventional CMOS, as the microbolometers can be fabricated at temperatures below about 400 C.

Figure 10:
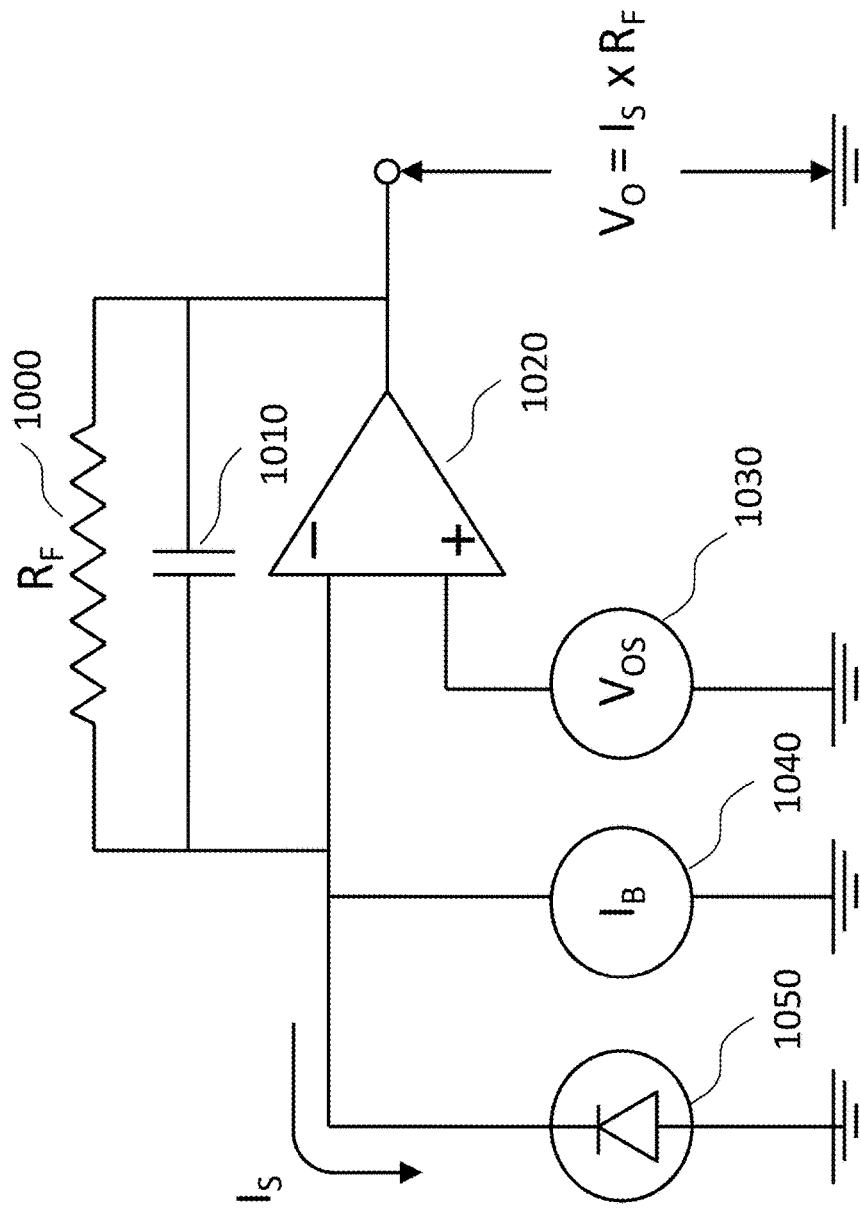
FIG. 10: The electrical schematics of the individual readout integrated circuit located under each photosensitive element in the sensor array.

Finally, the electrical schematic of ROIC element residing below each sensing pixel is given in FIG. 10. The signal from the photosensitive element 1050 is amplified with low noise amplifier 1020, having gain determined by the feedback loop consisting of resistor $R_f$, 1000 and the capacitor 1010. The circuit in FIG. 10 is driven by applied voltage $V_{OS}$ 1030 and applied current $I_b$ 1040. When the current generated by the photosensitive element 1050 is $I_S$, the amplified signal will be $V_O = I_S \times R_f$. Apart from the analog circuit, the analog to digital converter (ADC) is also included in each pixel in the preferred embodiment, even though row or column ADC's or single chip ADC can be used. In these cases, the readout of the data will be proportionately slower by a factor equal to the number of rows or columns or to the number of pixels.

Other embodiments of the optical sensing array architectures include

1. Different sensing arrays, with or without cooling (e.g. thermoelectric), InGaAs, HgCdTe, Si, microbolometers, different array sizes and dimensions and different packaging for central, edge and corner illumination. The arrays can be two dimensional (2D) or one dimensional (1D) and are placed in contact or in close proximity to the tested surface.
2. Different light sources. Apart from black body radiation sources, single light emitting diode (LED), array of LED's, SLD's, solid state lasers or solid state lasers in combination with fluorescent materials can be used to provide much higher illumination intensities in selected parts of spectrum to detect species of interest with higher sensitivities.
3. Different interferometers including Fourier Transform interferometers, such as infrared version of such an instrument (FTIR) or acousto-optic and photo-acoustic based spectrometers or tunable filter spectrometers.
4. Free space and fiber based illumination. Illumination can contain elements that are diffractive, refractive or graded index lens type or reflective optical elements. The illumination can employ the single or multiple beams.
5. Refractive index matching liquid between the last optical illumination element and the sample and the optical detection element(s) and the sample surface.

Different features from one architecture can be substituted into another architecture. For example, the black body light source 100 in FIG. 1 can be used in the third architecture in FIG. 2 instead of LED array or laser with fluorescent dies 200.

Advantages of the contact sensing array architectures include
a. Maximum light illumination efficiency and maximum collection light efficiency.
b. Highest detection efficiency with minimal signal lost between the sample surface and detector surface.
c. Most efficient rejection of background light—scattered, specularly and diffusely reflected from rough, inhomogeneous surfaces and interfaces.
d. Lowest electronic noise due to direct integration of electronics with detectors.
e. Highest data acquisition throughput with simultaneous data acquisition from multiple spectral channels.
f. Simultaneous acquisition in the whole spectral range.
g. Low detector and system cost with wafer level packaging option.
h. Optional substitution of interferometry with tunable light sources or filter arrays.
i. Fastest data acquisition times—parallel, simultaneous acquisition and data processing of all sensing elements, limited only by scanning speed of interferometer or laser tuning and required signal-to-noise ratio.
j. Mobile compatibility—small size, low power consumption, low cost and insensitivity to environmental factors, including temperature, humidity, shock and vibration.

The above described sensing systems based on sensing array architectures can be applied in routine non-invasive glucose monitoring, in assessment of subsurface infections, in sensing concentration of critical drugs in the body and in other areas of personalized wellness and medicine, in monitoring surface and subsurface contamination of food and in many other areas.

Figure 11B:
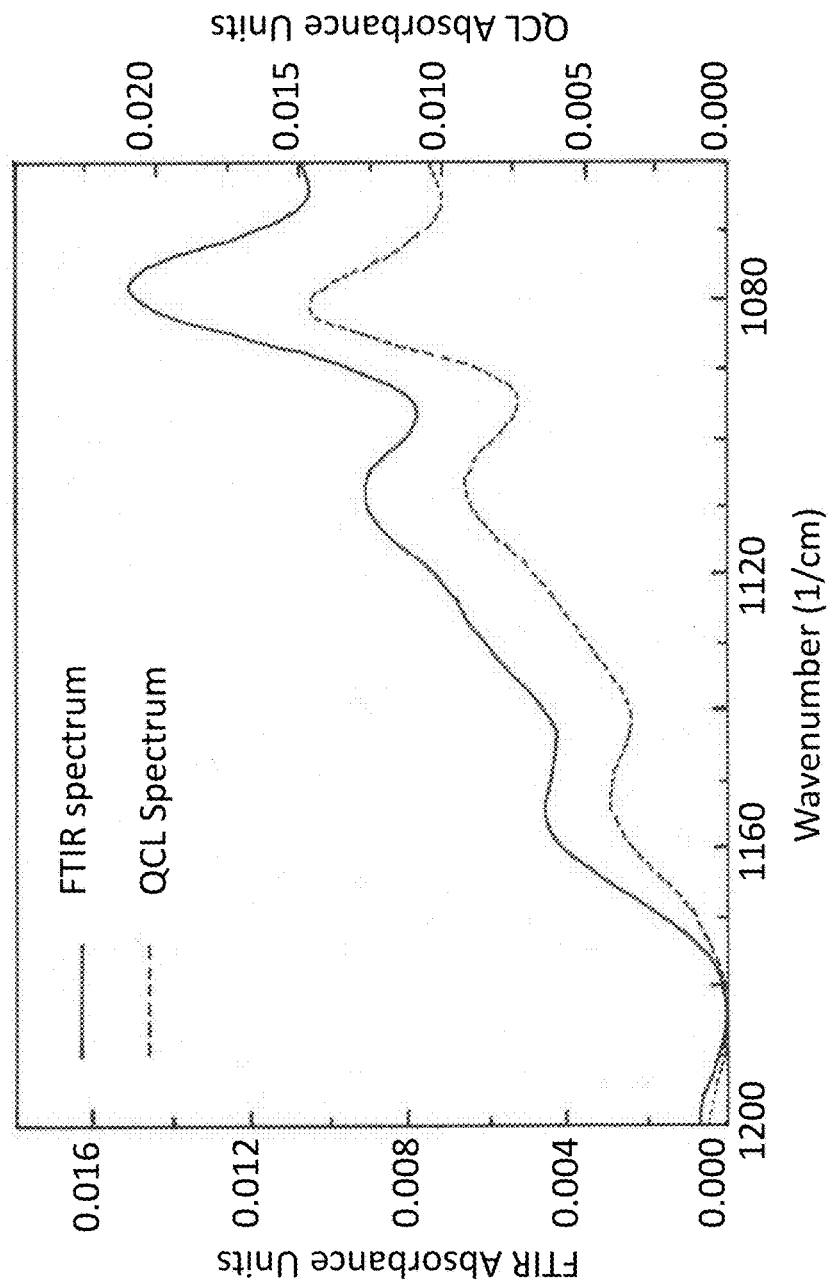
FIG. 11b: Mid infrared spectra of glucose.

Only application to noninvasive glucose monitoring will be described. The spectra of glucose are included in FIGS. 11a and 11b together with water spectra and interfering species spectra in near infrared (8000 to 4000 cm-1) and mid infrared (3 to 15 um) spectral regions. The data is acquired with detector array based optical engine with multiple optical paths and depths and analyzed with proprietary algorithms to yield the concentration of the glucose in the presence of many interfering species that are present at much higher concentration than glucose. The typical performance gives detectability limits <5 mg/dL, dynamic range extending past 300 mg/dL and accuracy of better than 3 mg/dL.

The optical engines described above are incorporated into the monitoring system that contains additional data processing and transfer capabilities, local storage or storage and processing in cloud and displays. Data transfer and communication capabilities are either wireless or wire line. The system provides feedback and tracking of concentration of species of interest with applications in personal health, wellness and fitness, food testing, etc. The monitoring system can also be used in the device that provides required medication to the user by activating the delivery system according to the feedback provided by difference between the required and measured levels.

What is claimed is:
1. An optical sensing engine comprising:
   an illumination system having a light source, an optical Fourier Transform interferometer and optical elements and providing a single, stationary light beam on a sample surface;
   a sensor array having multiple sensors configured to detect optical spectra corresponding to different optical paths from a sample, wherein the sensor array is in contact or proximity of the sample surface; and
   an acquisition system configured to capture multiple optical spectra simultaneously corresponding to different optical path lengths through the sample to the multiple sensors.
2. The optical sensing engine of claim 1, wherein the illumination system includes the light beam in central, edge or corner configuration with respect to the sensor array.
3. The optical sensing engine of claim 1, wherein the light source is a black body radiation source or a light emitting diode array or a laser in combination with a fluorescent dye.
4. The optical sensing engine of claim 1, wherein the optical Fourier Transform interferometer includes a moving mirror or integrated fiber optics or a double pendulum architecture.
5. The optical sensing engine of claim 1 wherein the sensor array is monolithically integrated with a CMOS electronics array or bonded to a matching CMOS electronics array or connected to a separate electronic circuit.
6. The optical sensing engine of claim 1, wherein the sensor array includes photosensitive material InGaAs, Si, or HgCdTe or a thermal sensor of microbolometer type.
7. The optical sensing engine of claim 1, the sensor array further comprising a segmented window with light reflecting or absorbing walls.
8. A method of detecting species of interest in the sample using spectral and spatial data obtained using the optical sensing engine of claim 1 and processing algorithms.
9. An optical monitoring system comprising of the optical sensing engine of claim 1, controller with processing electronics and display, storage and communication capabilities.
10. An optical sensing engine comprising:
    an illumination system having a light source, an optical Fourier Transform interferometer and optical elements with a last optical element of the illumination system in contact with a sample surface and providing a single, stationary light beam on a sample surface;
    a sensor array having multiple sensors configured to detect optical spectra corresponding to different optical paths from a sample, wherein the sensor array is in contact or proximity of the sample surface; and
    an acquisition system configured to capture multiple optical spectra simultaneously corresponding to different optical path lengths through the sample to the multiple sensors.
11. The optical sensing engine of claim 10, wherein the illumination system includes the light beam in central, edge or corner configuration with respect to the sensor array.
12. An optical sensing engine comprising:
    an illumination system having a tunable light source and optical elements and providing a single, stationary light beam on a sample surface;
    a sensor array having multiple sensors configured to detect optical spectra corresponding to different optical paths from a sample, wherein the sensor array is in contact or proximity of the sample surface; and
    an acquisition system configured to capture multiple optical spectra simultaneously corresponding to different optical path lengths through the sample to the multiple sensors.
13. The optical sensing engine of claim 12, wherein the sensor array includes photosensitive material InGaAs, Si, or HgCdTe or a thermal sensor of microbolometer type.

14. The optical sensing engine of claim 12, the sensor array further comprising a segmented window with light reflecting or absorbing walls.

15. A method of detecting species of interest in the sample using spectral and spatial data obtained using the optical sensing engine of claim 12 and processing algorithms.

16. An optical monitoring system comprising of the optical sensing engine of claim 12, controller with processing electronics and display, storage and communication capabilities.

17. An optical sensing engine comprising:

an illumination system having a light source and optical elements and providing a single, stationary light beam on a sample surface;

sensor arrays having multiple sensors and optical filter arrays, wherein each sensor and optical filter array detects optical spectra corresponding to different optical paths from a sample, wherein the sensor array is in contact or proximity of the sample surface; and an acquisition system configured to capture multiple optical spectra simultaneously corresponding to different optical path lengths through the sample to the multiple sensors.

18. The optical sensing engine of claim 12, wherein the sensor array is monolithically integrated with a CMOS electronics array or bonded to matching a CMOS electronics array or connected to a separate electronic circuit.

19. The optical sensing engine of claim 17, wherein the sensor array includes photosensitive material InGaAs, Si, or HgCdTe or a thermal sensor of microbolometer type.

20. The optical sensing engine of claim 17, the sensor array further comprising a segmented window with light reflecting or absorbing walls.

21. A method of detecting species of interest in the sample using spectral and spatial data obtained using the optical sensing engine of claim 17 and processing algorithms.

22. An optical monitoring system comprising of the optical sensing engine of claim 17, controller with processing electronics and display, storage and communication capabilities.

* * * * *